United States Patent [19]
Shmulewitz et al.

[11] Patent Number: 6,095,987
[45] Date of Patent: Aug. 1, 2000

[54] APPARATUS AND METHODS OF BIOELECTRICAL IMPEDANCE ANALYSIS OF BLOOD FLOW

[75] Inventors: Ascher Shmulewitz, Tel Aviv, Israel; Arthur A. Wallace, San Rafael, Calif.

[73] Assignee: Imagyn Medical Techonologies California, Inc., Newport Beach, Calif.

[21] Appl. No.: 08/934,036

[22] Filed: Sep. 19, 1997

Related U.S. Application Data

[63] Continuation of application No. PCT/US97/06369, Apr. 17, 1997, and a continuation-in-part of application No. 08/726,822, Oct. 4, 1996, Pat. No. 5,782,774, which is a continuation of application No. 08/634,758, Apr. 17, 1996, Pat. No. 5,791,346.

[51] Int. Cl.$^7$ ........................................................... A61B 5/05
[52] U.S. Cl. ............................ 600/547; 600/506; 600/509
[58] Field of Search ................................... 600/546, 547, 600/508, 509, 587, 506

[56] References Cited

U.S. PATENT DOCUMENTS

| | | | |
|---|---|---|---|
| 3,340,867 | 9/1967 | Kubicek et al. | 128/2.05 |
| 3,651,318 | 3/1972 | Czekajewski | 235/183 |
| 3,726,269 | 4/1973 | Webster, Jr. | 128/2.05 F |
| 3,915,155 | 10/1975 | Jacobson et al. | 128/2.05 F |
| 4,437,469 | 3/1984 | Djordjevich et al. | 128/672 |
| 4,450,527 | 5/1984 | Sramek | 364/415 |
| 4,671,295 | 6/1987 | Abrams et al. | 128/663 |
| 4,722,327 | 2/1988 | Abrams et al. | 128/663 |
| 4,836,214 | 6/1989 | Sramek | 128/693 |
| 4,852,580 | 8/1989 | Wood | 128/693 |
| 4,870,578 | 9/1989 | Vysin et al. | 364/413.05 |
| 4,953,556 | 9/1990 | Evans | 128/671 |
| 4,967,759 | 11/1990 | Teves | 128/715 |
| 5,005,573 | 4/1991 | Buchanan | 128/207.14 |
| 5,024,228 | 6/1991 | Goldstone et al. | 128/642 |
| 5,080,107 | 1/1992 | Teves | 128/773 |
| 5,125,406 | 6/1992 | Goldstone et al. | 128/642 |
| 5,203,344 | 4/1993 | Scheltinga et al. | 128/734 |
| 5,379,765 | 1/1995 | Kajiwara et al. | 128/642 |
| 5,453,086 | 9/1995 | Weber | 604/20 |
| 5,469,859 | 11/1995 | Tsoglin et al. | 128/723 |
| 5,477,860 | 12/1995 | Essen-Moller | 128/716 |

OTHER PUBLICATIONS

"Bioelectrical Impedance Analysis in Body Composition Measurement", *National Institute of Health Technology Assessment Conference Statement*, Dec. 12–14, 1994, pp. 3–35.

"Continuous Cardiac Output Monitoring Electrical Bioimpedance", *American College of Cardiology*, Jun. 1988, pp. 1–7.

B. Bhattacharya et al., "Potential Distribution in the Thorax in Relation to Electrical Field Plethysmography", *Medical & Biological Engineering & Computing*, May 1988, pp. 303–309.

F.H. Bonjer, M.D., et al., "The Origin of the Variations of Body Impedance Occurring During the Cardiac Cycle", *Circulation*, vol. VI, Sep. 1952, pp. 415–420.

(List continued on next page.)

*Primary Examiner*—John P. Lacyk
*Assistant Examiner*—Pamela L. Wingood
*Attorney, Agent, or Firm*—Fish & Neave; Nicola A. Pisano

[57] ABSTRACT

Apparatus and methods are provided for monitoring cardiac output using bioelectrical impedance techniques in which first and second electrodes are placed in the trachea and/or bronchus in the vicinity of the ascending aorta, while an excitation current is injected into the thorax via first and second current electrodes, so that bioelectrical impedance measurements based on the voltage drop sensed by the first and second electrodes reflect voltage changes induced primarily by blood flow dynamics, rather than respiratory or non-cardiac related physiological effects. Additional sense electrodes may be provided, either internally, or externally, for which bioelectrical impedance values may be obtained. Methods are provided for computing cardiac output from bioelectrical impedance values. Apparatus and methods are also provided so that the measured cardiac output may be used to control administration of intravenous fluids to an organism or to optimize a heart rate controlled by a pacemaker.

38 Claims, 6 Drawing Sheets

OTHER PUBLICATIONS

David E. Clarke, M.D., et al. "Thoracic Electrical Bioimpedance Measurement of Cardiac Output–Not Ready for Prime Time", *Critical Care Medicine*, vol. 21, No. 8, Aug. 1993, pp. 1111–1112.

H. Fuller, et al., "The Current Status and Future Directions of Impedance Cardiography in ICU", *Annals of Biomedical Engineering*, vol. 17, 1989, pp. 483–493.

David B. Geselowitz, "An Application of Electrocardiographic Lead Theory to Impedance Plethysomography", *IEEE Transactions on Bio–Medical Engineering*, vol. BME–18, No. 1, Jan. 1971, pp. 38–41.

Joseph C. Greenfield, Jr., M.D., et al., "Relation Between Pressure and Diameter in the Ascending Aorta of Man", *Circulation Research*, vol. X, May 1962, pp. 778–781.

Harry Handelsman, D.O., "Public Health Service Assessment Cardiac Output by Electrical Bioimpedance", *Health Technology Assessment Reports: Cardiac Output by Electrical Bioimpedance*, No. 3, 1989, pp. 1–5.

Deok W. Kim et al, "Origins of the Impedance Change in Impedance Cardiography by a Three–Dimensional Finite Element Model", *IEEE*, 1988, pp. 993–1000.

W.G. Kubicek, "On the source of Peak First Time Derivative (dZ/dt) During Impedance Cardiography", *Annals of Biomedical Engineering*, vol. 17, 1989, pp. 459–462.

John Lehr, "A Vector Derivation Useful in Impedance Plethysmographic Field Calculations", *IEEE Transactions on Biomedical Engineering*, Mar. 1972, pp. 156–157.

"Henry C. Lukaski. PhD, et al., Estimation of body Fluid Volumes Using Tetrapolar Bioelectrical Impedance Measurements", *Aviation, Space and Environmental Medicine*, Dec. 1998, pp. 1163–1169.

Daniel S. Miles, PhD et al., "Impedance Cardiography: Noninvasive Assessment of Human central Hemodynamics at Rest and During Exercise", *Exercise and Sport Sciences Reviews*, vol. 17, 1989, pp. 231–263.

Christos G. Pappas, M.D. et al., "Impedance Cardiography in the Measurement of Cardiac Output: Studies in Rabbits", *Journal of Surgical Research*, 59, 1995, pp. 504–510.

R.P. Patterson, "Fundamentals of Impedance Cardiography", *IEEE Engineering in Medicine and Biology Magazine*, Mar. 1989, pp. 35–38.

Bill C. Penney, PhD., et al., "An Overview of the Theory and Some Applications of Impedance Plethysmography", *IEEE Frontiers of Engineering in Health Care*, 1981, pp. 169–173.

Andrew Sherwood et al., "Committee Report; Methodological Guidelines for Impedance Cardiography", *Psychophysiology*, Feb. 1989, pp. 1–38.

William C. Shoemaker, MD, FCCM, et al., "Multicenter Trial of a New Thoracic Electrical Bioimpedance Device for Cardiac Output Estimation", *Critical Care Medicine*, vol. 22, No. 12, 1994, pp. 1907–1912.

Joseph M. VanDeWater, M.D. et al., "Development and Evaluation of a New Impedance Cardiograph", *Journal of Clinical Engineering*, May/Jun. 1995, pp. 218–223.

Li Wang, "Contributions of Heart Movement and Blood Volume Change to Impedance Cardiography Calculated by Human Thorax Models", *IEEE*, 1993, pp. 808–809.

Li Wang, "Multiple Sources of the Impedance Cardiograph Based on 3–D Finite Difference Human Thorax Models", *IEEE*, 1995, pp. 141–148.

Klaas R. Visser, Electrical Properties of Flowing Blood and Impedance Cardiography, *Annals of Biomedical Engineering*, vol. 17, 1989, pp. 463–473.

Xiang Wang, PhD et al., "Time–Frequency Distribution Technique in Biological Signal Processing", *Biomedical Instrumentation & Technology*, May–Jun. 1995, pp. 203–212.

APPARATUS AND METHODS OF BIOELECTRICAL IMPEDANCE ANALYSIS OF BLOOD FLOW

REFERENCE TO RELATED APPLICATIONS

This application claims priority of International Application PCT/US97/06369, filed Apr. 17, 1997, and is a continuation-in-part of U.S. patent application Ser. No. 08/726,822, filed Oct. 4, 1996, entitled "APPARATUS AND METHODS OF BIOELECTRICAL IMPEDANCE OF BLOOD FLOW," now U.S. Pat. No. 5,782,774 which is a continuation-in-part of U.S. patent application Ser. No. 08/634,758, filed Apr. 17, 1996, entitled "APPARATUS AND METHODS OF BIOELECTRICAL IMPEDANCE OF BLOOD FLOW,"now U.S. Pat. No. 5,791,346.

FIELD OF THE INVENTION

The present invention relates generally to apparatus and methods for non-invasively measuring cardiac output and, more particularly, to apparatus and methods for measuring cardiac output using bioelectrical impedance analysis techniques.

BACKGROUND OF THE INVENTION

Knowledge of cardiac output is crucial in the care of critically ill patients, as well as patients with chronic heart disease requiring monitoring of medication. For many years the standard of cardiac output measurement has been pulmonary artery catheterization. Previously known catheterization techniques, as described, for example, in U.S. Pat. Nos. 3,915,155, 3,726,269 and 3,651,318, involve periodic injection into the patient's bloodstream of a bolus of heated saline, during which thermodilution measurements are performed to determine cardiac output. Such techniques cannot generally be used for continuous monitoring. Moreover, such catheterization techniques pose significant risk to the patient, including malignant arrhythmias, pulmonary artery rupture, and in rare cases, death.

Consequently, for many years work has been underway to develop less invasive apparatus and methods for monitoring cardiac output. For example, as an alternative to catheterization methods, Doppler ultrasound techniques have been adapted to measure the velocity of blood flow. If the diameter of a vessel, its flow profile, and the angle of the ultrasound beam relative to the vessel can be determined, Doppler ultrasound measurements of the ascending aorta, either externally (from the suprasternal notch) or internally (from within the trachea) can be used as a measure of cardiac output.

U.S. Pat. No. 4,671,295 describes an example of such methods and apparatus, wherein an ultrasound transducer is mounted on the tip of an endotracheal tube so that Doppler measurements of blood flow from a point (pulse wave mode) or path (continuous wave mode) along the ultrasound beam can be measured. The method described in the patent requires multiple measurements within the blood vessel, a priori knowledge of the blood flow pattern and cross-sectional area of the vessel, and the relative angulation of the blood vessel. In addition, the measurement is highly dependent upon the exact placement of the transducer. These drawbacks have resulted in the slow adoption of Doppler ultrasound cardiac output techniques.

A yet further technique which the prior art has sought to apply to the measurement of cardiac output is bioelectrical impedance analysis ("BIA"). BIA has recently gained wide use as a method for measuring body composition and physiological metrics. BIA involves passing a low level electrical alternating current ("AC") through body tissues between multiple electrodes, measuring the voltage difference between multiple locations on the tissue, and then calculating the electrical impedance (electrical resistance plus reactance) of the stimulated tissue.

Generally, BIA apparatus employ two current electrodes to conduct a low level excitation current through body tissue. As current flows in the tissue, a potential difference develops across the tissue which is proportional to the value of the AC current and the tissue impedance. The tissue impedance may be calculated by disposing two sense electrodes between the current electrodes and measuring the voltage difference between the two sense electrodes.

Current flows predominantly through body materials with high conductivity, such as blood. Less current flows through muscle, which has an intermediate conductivity, while the conductivity of fat, air and bone is much lower than that of either blood or muscle. Because the resistance to current flow is a function of the conductivity and cross-sectional area of the conducting volume, volumes having a larger cross-sectional area have lower electrical resistance.

It is also known that the impedance of the conducting volume and the measured medium metrics (i.e., static parameters such as fat or water content, and dynamic metrics, such as blood flow) are dependent upon the placement of the electrodes and the conducting path between the electrodes. Thus, the greater the distance between the electrodes, the more likely that extraneous variables will affect the measurement.

Previously known BIA methods generally correlate the measured voltage drop between the sense electrodes to tissue impedance using relatively simple algorithms based on simplified models of body structure, for example, by assuming that the body is composed of simple cylindrical resistive volumes. Temporal cyclical variations in the body impedance are then assumed to result from physiological events such as blood flow and breathing.

Measurements of the electrical impedance, and particularly, the time-varying nature of electrical impedance, may therefore provide a non-invasive indicator of physiological events. Various algorithms have been developed to isolate specific physiological parameters, such as cardiac output, from the measured bioelectrical impedance, as described, for example, in W. G. Kubicek, et al., "Development And Evaluation Of An Impedance Cardiac Output System," *Aerospace Medicine*, Vol. 37, pp. 1208–1212 (1966) and U.S. Pat. No. 3,340,862, which is incorporated herein by reference.

Despite the application of BIA methods for measuring cardiac output, no simple continuous BIA based cardiac output measurement device has gained widespread acceptance. Many existing BIA devices use external or internal electrodes to measure bioelectrical impedance for large volumes, for example, the whole body or thoracic segments. Because the excitation current diffuses throughout the entire volume, making use of any and all conductive paths, differences between individual patients, and even for the same patient over time, may inhibit standardizing the BIA metrics.

Moreover, it is known that while BIA measurements of cardiac output provide good correlation for normal patients and those hemodynamically stable patients, there is poorer correlation for critically ill patients and patients in heart failure, as described, for example, in R. J. Detemeter et al., "The Use Of Noninvasive Bioelectric Impedance To Determine Cardiac Output: Factors Affecting Its Accuracy," *Am. J. Noninvasive Cardiol.,* Vol. 2, pp. 112–118 (1988).

An example of an attempt to overcome the variabilities encountered when taking bioelectrical impedance measurements across large volumes is described, for example, in U.S. Pat. No. 4,870,578. That patent describes BIA apparatus for monitoring cardiac output by using external electrodes that measure the electrical resistance of a segment of the thorax and includes circuitry to account for respiratory-induced voltage changes. As acknowledged in that patent, the respiratory-induced voltage changes are typically much greater than the cardiac-induced voltage changes.

Other devices that attempt to account for the effect of non-cardiac physiological events on bioelectrical impedance include arranging multiple electrodes on esophageal catheters to measure thoracic bioelectric impedance, as described, for example, in U.S. Pat. Nos. 4,852,580 and 4,836,214. Both patents describe multi-electrode arrays inserted into the esophagus to provide an impedance measurement reflecting blood flow in the descending aorta. Such devices are not believed to provide true isolation of cardiac-induced voltage changes from those induced by other physiological events. In addition, these systems do not ensure that the multiple electrodes make positive contact with the esophageal wall.

BIA measurements have also been employed to provide a metric of cardiac output by measuring physiologic effects other than blood flow. For example, U.S. Pat. No. 4,953,556 describes a BIA arrangement including an internal electrode mounted on an esophageal catheter and an external electrode which is disposed above the apex of the heart. The apparatus described in that patent attempts to use BIA measurements to determine cardiac wall motion and lung motion, from which an estimate of cardiac output and pulmonary activity can be obtained.

In view of the foregoing, it would be desirable to provide apparatus and methods for accurately, non-invasively and continuously measuring cardiac output using BIA techniques.

It further would be desirable to provide apparatus and methods for measuring cardiac output in critically ill patients using BIA techniques that overcome the inaccuracies arising from measuring voltage changes across whole body or large volume thoracic segments.

It also would be desirable to provide inexpensive apparatus and methods for measuring cardiac output using BIA techniques that overcome the drawbacks of previously known BIA cardiac output measurement devices and methods.

It would further be desirable to provide apparatus and methods for continuously monitoring cardiac output so as to permit the measured cardiac output to be employed as a metric for controlling and maintaining other aspects of a patient's health.

SUMMARY OF THE INVENTION

In view of the foregoing, it is an object of this invention to provide apparatus and methods for accurately, non-invasively and continuously measuring cardiac output using BIA techniques.

It is another object of this invention to provide apparatus and methods for measuring cardiac output in critically ill patients using BIA techniques that overcome the inaccuracies arising from measuring voltage changes across the whole body or large volume thoracic segments.

It is yet another object of the present invention to provide inexpensive apparatus and methods for measuring cardiac output using BIA techniques that overcome the drawbacks of previously known BIA cardiac output measurement devices and methods.

It is still another object of this invention to provide apparatus and methods for continuously monitoring cardiac output that permit the measured cardiac output to be employed as a metric for controlling and maintaining other aspects of a patient's health.

These and other objects of the invention are accomplished in accordance with the principles of the invention by providing BIA cardiac output monitoring apparatus that can be disposed within a patient's airway (e.g., trachea and/or bronchus) in close relation to the ascending aorta to acquire cardiac output information. Apparatus in accordance with the present invention includes: 1) one or more sense electrodes placed in the patient's trachea in the vicinity of the ascending aorta; 2) at least two current electrodes disposed either on an exterior surface of the patient's thorax or within the patient's trachea; and 3) optionally, at least one sense electrode disposed on the patient's exterior surface in the vicinity of the suprasternal notch.

In accordance with the principles of the invention, current conducted between the current electrodes flows throughout the thorax, and passes preferentially through blood because of its high conductivity, relative to other body materials. The sense electrodes primarily sense the voltage drop in the blood in the ascending aorta. Because the impedance of the blood in the aorta changes with the volume of blood flowing through the aorta, the measured voltage drop between the sense electrodes varies with blood flow. The time-varying differences in the sensed voltage, therefore, are primarily caused by blood flow dynamics, rather than respiratory or non-cardiac related physiological effects.

Methods in accordance with the present invention overcome the inaccuracies of the gross physiologic models employed in previously known BIA cardiac methods, by avoiding the simplified algorithms for the ventricular stroke volume based on whole thorax BIA measurements. In particular, the methods of the present invention avoid the inaccuracies in whole body or thoracic BIA measurements associated with ignoring the multiple, branched and complex paths of blood flow.

In accordance with the present invention, the ability to obtain BIA measurements in the vicinity of the ascending aorta, which has no branches other than the coronary arteries, and which therefore closely reflects the blood flow through the ascending aorta, provides a simple and highly accurate metric for computing ventricular stroke volume.

In yet further aspects of the present invention, the apparatus for monitoring a patient's cardiac output may be used to control administration of intravenous fluids to a patient or to optimize heart rate for those patients having pacemakers.

BRIEF DESCRIPTION OF THE DRAWINGS

Further features of the invention, its nature and various advantages will be more-apparent from the accompanying drawings and the following detailed description of the preferred embodiments.

DETAILED DESCRIPTION OF THE INVENTION

The present invention relates generally to BIA apparatus for use in measuring cardiac output in patients, including critically ill and heart-diseased patients, as well as patients undergoing elective surgery. The apparatus and methods of the present invention overcome drawbacks observed in previously known attempts to use whole body or large volume thoracic BIA measurements to measure cardiac output, by providing apparatus and methods that are not based upon the gross modeling of physiological events implicit in such previously known BIA measurement techniques.

In a first family of embodiments of the apparatus and methods of the present invention, two or more sense electrodes are disposed in contact with a patient's airway (trachea and/or bronchus) in close relation to and along the axis of the ascending aorta, so that changes in bioelectrical impedance can be closely correlated to cardiac events, without significant effects due to non-cardiac physiologic events. Excitation AC current is injected into the body between two or more current electrodes disposed on the exterior of the patient's thorax. In a second family of embodiments constructed in accordance with the present invention, the excitation current is injected into the patient's thorax by current electrodes disposed in the patient's airway, preferably in the vicinity of the pharynx and bronchus.

In both families of embodiments, bioelectrical impedance is computed from the voltage drop measured either between two or more of the sense electrodes disposed in the patient's airway or one or more of the sense electrodes disposed in the patient's airway and one or more external electrodes disposed in the vicinity of the patient's suprasternal notch. The value of bioelectrical impedance is in turn correlated to blood flow through the ascending aorta. Because the ascending aorta has no other branches other than the coronary arteries, blood flow through the ascending aorta may be closely correlated to cardiac output.

It is known in the medical literature that BIA measurements of cardiac output in general show good correlation for normal patients and hemodynamically stable patients, but much poorer correlation for critically ill patients, and patients in heart failure, as discussed in the above-mentioned Detemeter paper. Applicant has discovered that the reason for this poorer correlation in the latter cases is that the theoretical basis underlying the use of whole body or large volume thoracic measurements may be incorrect.

While the present invention finds ready application in monitoring cardiac output in critically-ill and heart diseased patients, it may be advantageously used for all intubated patients, including pediatric cases. For example, apparatus constructed in accordance with the present invention may be readily employed in asymptomatic patients undergoing elective surgery. As many as 95% of postoperative deaths in the latter population result from hemodynamic failure.

Previously known techniques derive the equation for ventricular stroke volume ("SV") from the assumption that a time-varying column of blood, in parallel with the other conducting material in the thorax, changes from zero to the full stroke volume during the cardiac cycle. The column of blood is assumed to be the length between the electrodes used to obtain the BIA measurements, with effects on the BIA measurements due to respiration accounted for, for example, as discussed in the aforementioned U.S. Pat. No. 4,870,578.

Figure 1A:
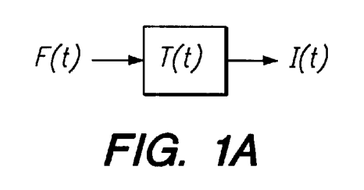
FIGS. 1A and 1B are idealized models of the volumes upon which previously known bioelectrical impedance algorithms are based.

FIG. 1A illustrates a typical previously known BIA algorithm. Cardiac output is estimated from the bioelectrical impedance measurement I(t), where it is assumed that changes in the bioelectrical impedance coincidental with the heart electrical activity (as represented by an electrocardiograph output) are the result of blood flow F(t). A transfer function T(t) is then based upon empirical formulae derived from measurements taken on healthy, hemodynamically stable subjects. The bioelectrical impedance I(t) is then computed as:

$$I(t)=F(T)*T(t) \qquad (1)$$

Applicant has determined, however, that the foregoing assumption regarding the column of blood ignores the branched, multiple and complex paths present in the arterial system. Moreover, the distribution of blood and fluids between different physiologic "compartments" in the idealized thoracic or whole body model and body regions are different in normal and critically ill patients.

Figure 1B:
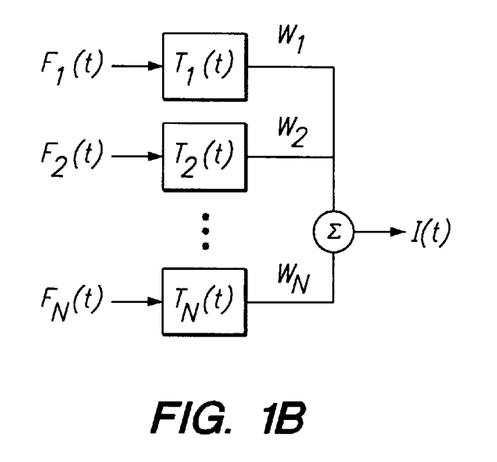

FIG. 1B illustrates that the thoracic approach to BIA measurement must account for transfer functions appropriate to each of the multiple blood flow paths through the volume, so that bioelectrical impedance I(t) should be computed as:

$$I(t)=\Sigma F_i(t)*T_i(t)*W_i \qquad (2)$$

where $W_i$ are weights corresponding to a priori knowledge of the relative distribution of flow through the various segments of the volume, e.g., the aorta, and arterial segments and other fluid chambers. Moreover, the weights $W_i$ may be different for different patients, may be different for chronically ill as opposed to healthy subjects, and may be variable even within a given patient, e.g., due to changes in heart rate.

Applicant has discovered, however, that equation (1) may be used accurately for any patient provided that the transfer function T(t) is correlated to measured blood flow (e.g., using a flow meter) so that the effect of the distribution weights $W_i$ can be essentially eliminated. Accordingly, applicant has concluded that BIA measurements should be taken very close to a major blood vessel or artery, so that between the electrodes of the BIA apparatus there are few or no branching vessels or adjacent vessels. The present invention therefore involves the use of BIA measurements in the vicinity of blood vessels meeting the foregoing requirements, especially the ascending aorta.

Figure 2A:
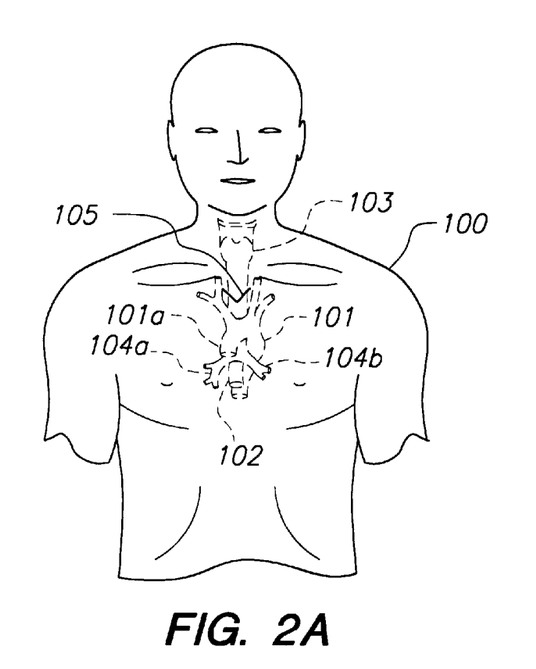
FIGS. 2A and 2B are a vertical frontal view of the upper portion of a human body and a front view of the ascending aorta, the esophagus and the trachea, respectively.
Figure 2B:
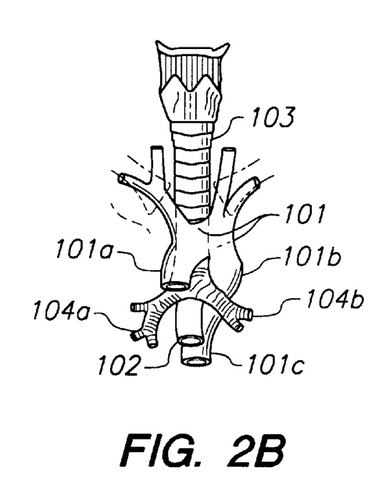

Referring to FIG. 2A, the upper portion of a human body 100 is shown in outline with the corresponding locations of aorta 101, esophagus 102, trachea 103, and bronchi 104a and 104b (all shown in dotted line) and suprasternal notch 105. These internal vessels and organs are more clearly depicted in FIG. 2B. With reference to FIGS. 2A and 2B, the outflow tract of the left ventricle of the heart is ascending aorta 101a. Segment 101b of the artery (the aortic arch) passes in front of right bronchus 104a, in front of trachea 103 and then arches behind left bronchus 104b into the descending aorta 101c, which leads towards the lower part of the body.

Applicant has observed that because ascending aorta 101a passes in close proximity to bronchi 104a and 104b and trachea 103, it is possible to obtain a BIA measurement across ascending aorta 101a, with relatively little intervening tissue, by positioning two or more internal, or internal and external, sense electrodes at this location. For example, a first sense electrode may be disposed in trachea 103 and a second sense electrode may be disposed on the patient's external surface near suprasternal notch 105. Alternatively, two or more sense electrodes may be positioned within trachea 103 aligned with the axis of ascending aorta 101a, so that at least a first sense electrode is disposed above aortic arch 101b and a second sense electrode is disposed at a level just below aortic arch 101b.

AC voltage applied to the patient's tissue by current electrodes, positioned either on the external surface of the patient or within the patient's airway, causes an AC current to flow in the patient's tissue. The measured voltage difference between the sense electrodes is then employed to compute tissue impedance. Because the first branches from the aorta (other than the coronary arteries) are from aortic arch 101b, downstream of the measurement location, the measurement of blood flow from ascending aorta 101a accurately measures the volume of blood ejected from the left ventricle.

Moreover, the calculated bioelectrical impedance I(t) in equation (1) comprises both a desired signal $S(t)=F(t)*T(t)$, due to aortic blood flow, and a noise component, N(t), caused by non-cardiac related physiological effects, such as body motion and respiratory effects. The signal-to-noise ratio ("SNR") is computed as:

$$SNR=S(t)/N(t) \tag{3}$$

Accurate measurement of cardiac output requires averaging repeated BIA measurements. If the SNR can be increased, however, less averaging is required to achieve accurate blood flow measurements. Applicant has observed that the SNR is affected by the position of the sense electrodes, and more particularly, that improved SNR may be attained by providing the sense electrodes with preferred orientations relative to the ascending aorta, as described in greater detail hereinbelow.

Apparatus of the present invention is described with respect to two families of embodiments. In the first family of embodiments, excitation AC current is applied to the patient's thorax by two or more current electrodes disposed on an external surface of the thorax; in a second family of embodiments, the current electrodes are disposed within the patient's airway. It is contemplated that the choice of placement of the current electrodes will not substantially effect the BIA values or corresponding cardiac output measurements. Rather, the choice of using internal versus external current electrodes relates to the particular use of the apparatus. For example, internal electrodes may be desirable to reduce the number of wires crossing a sterile operating field, while external electrodes may be desirable for certain short-term cardiac output monitoring situations.

Figures 3A, 3B, 3C:
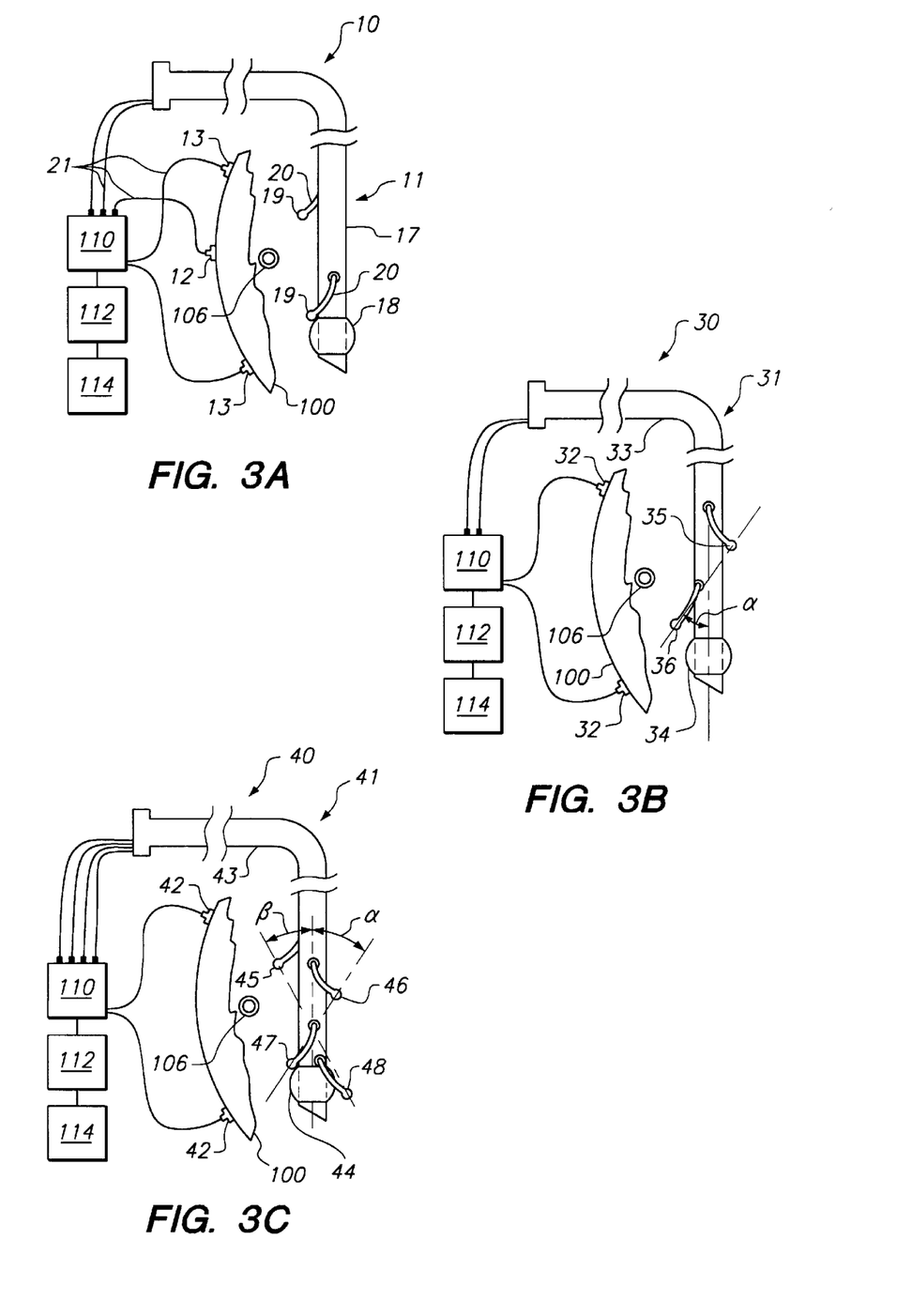
FIGS. 3A–3C are schematic views (including block diagrams) of members of a first family of embodiments of the present invention, wherein the current electrodes are disposed on an external surface of the patient's thorax.

Referring now to FIGS. 3A–3C, illustrative members of a first family of embodiments of the present invention are described. In FIG. 3A, apparatus 10 constructed in accordance with the principles of the present invention is described. Apparatus 10 includes sense electrode apparatus 11, external sense electrode 12, current electrodes 13, impedance recorder 110, digital sampler 112 and computer 114. In FIGS. 3, the patient's thorax is denoted by reference numeral 100 while the aortic arch is indicated in cross-section by reference numeral 106.

Sense electrode apparatus 11 comprises endotracheal tube 17 having inflatable cuff 18, a lumen for ventilating the patient, and at least one, and preferably two or more, sense electrodes 19. Sense electrodes 19 are carried on wires 20 slidably disposed in lumens of the endotracheal tube (as shown, for example, in FIG. 5B). Wires 20 deflect outwardly when moved to their deployed position, to urge sense electrodes 19 into contact with the interior surface of the trachea and/or the bronchi.

External sense electrode 12 is preferably disposed on the surface of the patient's thorax, in or near the suprasternal notch, while current electrodes 13 are disposed on an exterior surface of patient's thorax 100 at positions adequate to bracket the sense electrodes. External sense electrode 12 may comprise a spot EKG electrode, for example, model AMI 1750-001, manufactured by Medtronic-Andover Medical, Boston, Mass. Sense electrode apparatus 11, external sense electrode 12, and current electrodes 13 are coupled to impedance recorder 110 by electrical leads 21. Inflatable cuff 18 engages the interior wall of the trachea to retain and stabilize endotracheal tube 17 in position.

Impedance recorder 110 may be a commercially available impedance recorder providing both the current injected by current electrodes 13 (generally less than 1 mA at a frequency of 50–100 kHz) and impedance measuring capability, for example, the Minnesota Impedance Cardiograph Model 304A, operating at 100 kHz. Signals output from the impedance recorder are digitally sampled by digital sampler 112, for example, at a rate of 250 Hz using a standard 12-bit analog to digital converter, available from ComputerBoards, Inc., Mansfield, Mass. The sampled output of digital sampler 112 is then provided to computer 114, for example, an IBM-compatible personal computer having an Intel 386 or higher microprocessor, for storage and processing, as described hereinafter.

BIA measurements are obtained by injecting current through current electrodes 13 and measuring the voltage between a selected one of the sense electrodes 19 on sense electrode apparatus 11 and external sense electrode 12. In this manner, the voltage drop sensed by apparatus 10 corresponds primarily to that induced by blood flow changes through the ascending aorta. By providing two or more sense electrodes on endotracheal tube 17, sense electrode 19 closest to aortic arch 106 may be selected for use in combination with external sense electrode 12 to measure the voltages used in determining bioelectrical impedance. Thus, for example, the clinician may use combinations of external electrode 12 in combination with each of sense electrodes 19 in sequence, to determine which provides the strongest signal, and hence, the best measure of cardiac output.

Alternatively, the voltage drop between sense electrodes 19 may be used directly to compute bioelectrical impedance, without the use of external sense electrode 13. In this instance, endotracheal tube 17 is positioned within the trachea (using for example, radiographic markers disposed on the tube) so that one of sense electrodes 19 is located at a height even with, or slightly above, aortic arch 106, while another sense electrode 19 is disposed at a height just below the aortic arch. When two or more sense electrodes are provided on sense electrode apparatus, the clinician may evaluate various combinations of the sense electrodes to determine which provides the strongest signal.

Referring now to FIG. 3B, apparatus 30 is described. Apparatus 30 is similar to that of FIG. 3A, such as described in the preceding paragraph, and comprises sense electrode apparatus 31, current electrodes 32, impedance recorder 110, digital sampler 112 and computer 114. Sense electrode apparatus includes endotracheal tube 33 having inflatable cuff 34 and at least proximal and distal sense electrodes 35 and 36. In this embodiment, proximal and distal sense electrodes are arranged so that, when fully deployed, a line connecting the two electrodes forms an angle a with respect to the longitudinal axis of the endotracheal tube.

One of current electrodes 32 is applied to thorax 100 proximally of proximal sense electrode 35 while the other current electrode is applied to the thorax distally of distal electrode 36, so that the current electrodes bracket the sense electrodes. Current from impedance recorder 110 is injected into the patient's thorax 100 by current electrodes 32, and sensed by proximal and distal sense electrodes 35 and 36. The voltage drop between sense electrodes 35 and 36 is then employed to determine impedance.

In accordance with one aspect of the present invention, the angle a formed between sense electrodes 35 and 36 and the longitudinal axis of the endotracheal tube is preferably in a range of between 25 and 45degrees. Applicant has determined that orientation of the sense electrodes in this manner will account for angulation in the aortic anatomy. In particular, applicant expects that by positioning the proximal and distal sense electrodes at an angle with respect to endotracheal tube 31, the sense electrodes will be more nearly aligned with the axis of the ascending aorta, as opposed to the embodiment of FIG. 3A.

Referring now to FIG. 3C, apparatus 40 is described. Apparatus 40 constitutes a modified form of apparatus 30 of FIG. 3B, and comprises sense electrode apparatus 41, current electrodes 42, impedance recorder 110, digital sampler 112 and computer 114. Sense electrode apparatus 41 includes endotracheal tube 43 having inflatable cuff 44, proximal sense electrodes 45 and 46 and distal sense electrodes 47 and 48. Proximal sense electrode 46 and distal sense electrode 47 are arranged so that, when fully deployed, a line (accounting for the curvature of the endotracheal tube) connecting the two electrodes forms an angle a with respect to the longitudinal axis of the endotracheal tube. Proximal sense electrode 45 and distal sense electrode 48 are also arranged so that, when fully deployed, a line connecting the two electrodes forms an angle $\beta$ with respect to the longitudinal axis of the endotracheal tube. Current electrodes 42 are disposed on thorax 100 so as to bracket all of the sense electrodes on sense electrode apparatus 41.

The angle a formed between sense electrodes 46 and 47 and the longitudinal axis of the endotracheal tube is preferably in a range of between 25 and 45 degrees, while angle $\beta$ correspondingly is in a range of 65 to 45 degrees. Preferably, sense electrodes 45 and 48 are orthogonal to electrode pair 46 and 47. Thus, whereas sense electrodes 46 and 47 will be more nearly aligned with the axis of the ascending aorta ("on-axis"), sense electrode pair 45 and 48 will be oriented normal to the axis of the aorta ("normal-to-axis") and provide a signal effected by non-blood flow effects, such as respiratory effects and cardiac wall motion.

Accordingly, the voltage drop measured between sense electrodes 46 and 47 may be used to calculate an "on-axis" impedance, corresponding to blood flow through the ascending aorta and any non-cardiac effects, while the voltage drop measured between sense electrodes 45 and 48 may be used to calculate a "normal-to-axis" impedance that is expected to correspond primarily to non-blood flow effects. Applicant contemplates that by subtracting the normal-to-axis impedance from the on-axis impedance, the resulting impedance value will correspond predominantly to blood flow, and have a higher SNR than may be attained with the apparatus of FIGS. 3A or 3B.

Figure 4A:
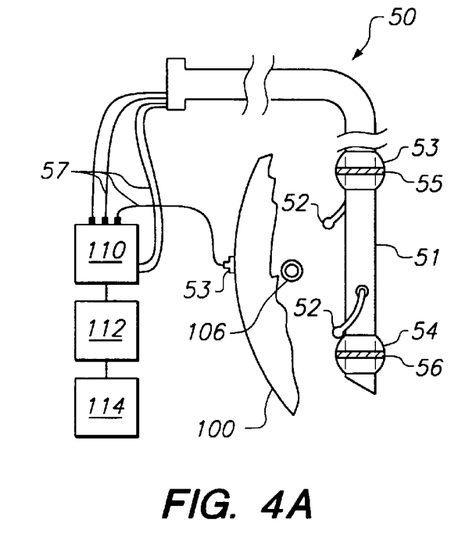
FIGS. 4A–4C are schematic views (including block diagrams) of members of a second family of embodiments of the present invention, wherein the current electrodes are disposed within the patient's airway.
Figure 4B:
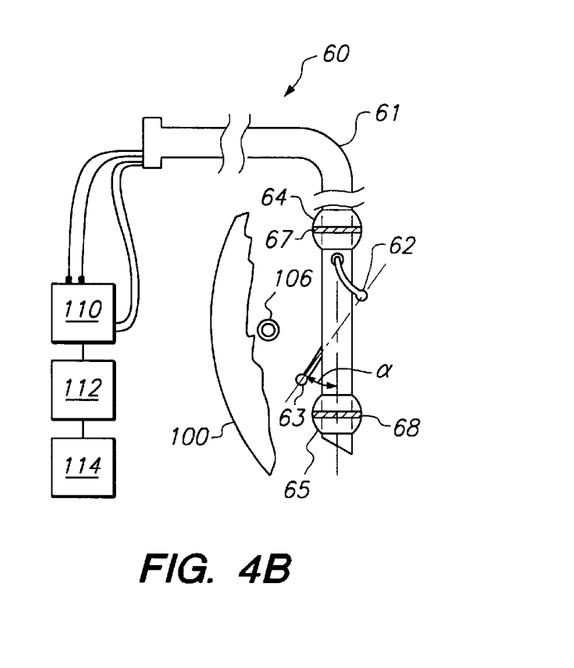
Figure 4C:
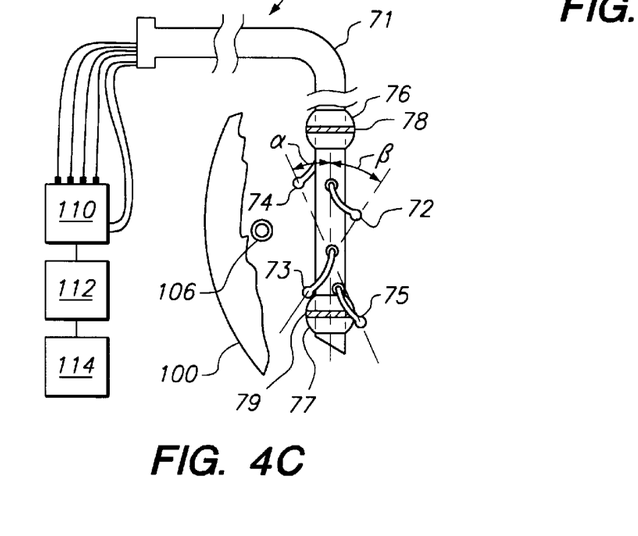

Referring now to FIGS. 4A–4C, the second family of embodiments of the present invention are described. In the following descriptions of FIGS. 4A–4C, impedance recorder 110, digital sampler 112, and computer 114 provide the same functionality as described hereinabove with respect to FIGS. 3, and will therefore be omitted from further detailed discussion.

With respect to FIG. 4A, a first illustrative member of the second family of embodiments of the present invention is described. Apparatus 50 is similar to that described above with respect to FIG. 3A, except that in apparatus 50 the current electrodes are disposed on the endotracheal tube, rather than the exterior surface of the thorax. In particular, apparatus 50 includes endotracheal tube 51, two or more sense electrodes 52, external sense electrode 53, inflatable cuffs 53 and 54, and proximal and distal current electrodes 55 and 56 mounted on inflatable cuffs 53 and 54, respectively. Electrodes 52, 53, 55 and 56 are coupled to impedance recorder 110 by leads 57.

Proximal current electrode 55 is disposed in the patient's trachea so that it contacts either the pharynx or larynx when inflatable cuff 55 is inflated. Distal current electrode 56 is disposed to contact the interior wall of the patient's trachea, for example, at a height below the xiphoid process, when inflatable cuff 54 is inflated. Current electrodes 55 and 56 conduct an AC excitation current from impedance recorder 110 to the patient's thorax.

Sense electrodes 52 and 53 may be employed as described hereinabove with respect to FIG. 3A. In particular, impedance values may be determined based upon either voltages measured between a selected one of sense electrodes 52 and external electrode 53, between sense electrodes 52 positioned above and below aortic arch 106, or a combination thereof.

In FIG. 4B, an alternative member of the second family of embodiments is described. Apparatus 60 mirrors apparatus 30 of FIG. 3B, except that apparatus 60 includes proximal and distal current electrodes 67 and 68 disposed on inflatable cuffs 64 and 65 respectively. Proximal and distal sense electrodes 62 and 63 are arranged so that, when fully deployed, a line between the two electrodes forms an angle a with respect to the longitudinal axis of endotracheal tube 61. Angle $\alpha$ preferably is in a range of between 25 to 45 degrees, so that the electrodes are more nearly aligned with the axis of the ascending aorta.

In FIG. 4C, a further alternative member of the second family of embodiments is described. Apparatus 70 is similar to that described above with respect to apparatus 40 of FIG. 3C. Apparatus 70 includes proximal and distal current electrodes as described with respect to FIG. 4B, and which operate in like manner to serve a like purpose. Apparatus 70 includes a pair of "on-axis" sense electrodes 72 and 73 and a pair of "normal-to-axis" electrodes 74 and 75, as described above with respect to FIG. 3C. Applicant expects that apparatus 70 will provide higher SNR than the embodiments of FIGS. 4A and 4B, because respiratory effects and wall motion artifacts may be removed from the impedances by taking differences between the "on-axis" voltage drop and the "normal-to-axis" voltage drop.

Figures 5A, 5B:
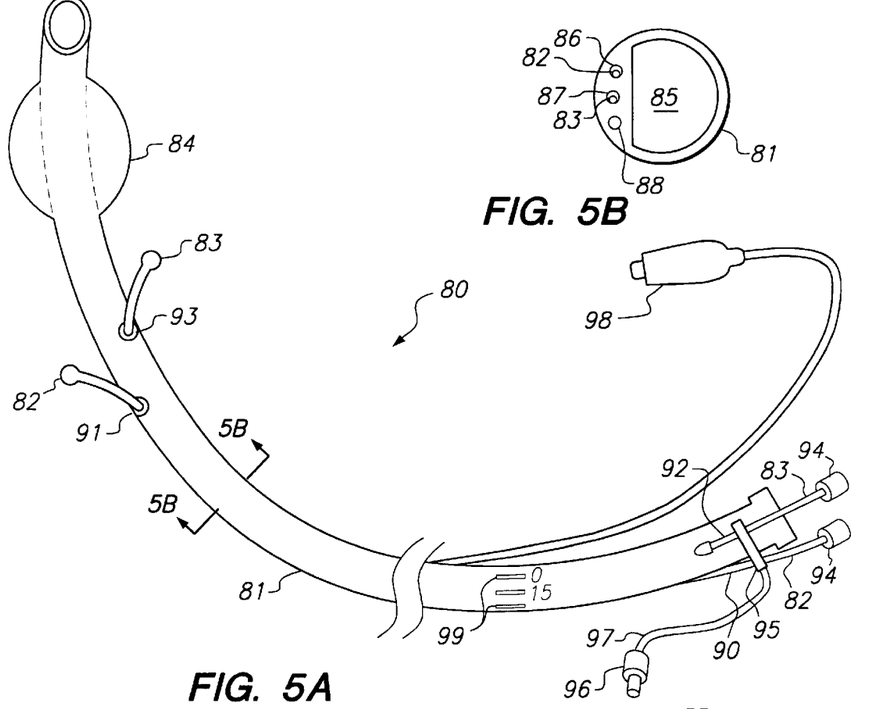
FIGS. 5A and 5B are, respectively, a perspective view and a cross-sectional view along view line 5B—5B, of an illustrative member of the first family of embodiments of the present invention.

Referring now to FIGS. 5A and 5B, an illustrative embodiment of sense electrode apparatus 80 similar to that of FIG. 3B is described in greater detail. Apparatus 80 comprises endotracheal tube 81 carrying proximal sense electrode 82, distal sense electrode 83, and inflatable cuff 84. As shown in FIG. 5B, endotracheal tube 81 includes lumen 85 for providing ventilation to the patient during intubation, lumen 86 through which proximal sense electrode 82 may be reciprocated, lumen 87 through which distal sense electrode 83 may be reciprocated, and lumen 88 for inflating inflatable cuff 84.

Sense electrodes 82 and 83 preferably comprise electrically insulated stainless steel wires about 0.020 inches (0.051 mm) thick that are pre-stressed to deflect outwardly when extended from lumens 86 and 87, thus urging the electrodes into contact with the interior wall of the patient's airway (e.g., trachea or bronchus). Each of sense electrodes 82 and 83 preferably includes an exposed ellipsoidal or spherical region at its distal end that provides an atraumatic tip. Sense electrodes are arranged so that, when fully deployed from lumens 86 and 87, a line between the tips of the electrodes preferably forms an angle in a range of between 25 and 45 degrees with respect to the longitudinal axis of the endotracheal tube.

Sense electrode 82 enters lumen 86 through opening 90 at the proximal end of endotracheal tube 81 and exits lumen 86 through skive 91 that opens to the lateral face of endotracheal tube 81. Sense electrode 83 enters lumen 87 through opening 92 and exits lumen 87 through skive 93 near the distal end of endotracheal tube 81. Each of the sense electrodes preferably includes a 0.0005 inch (0.013 mm) thick layer of insulation over the length of the electrode that extends outside of lumens 86 and 87, respectively, except that the ellipsoidal or spherical members at the distal ends of the electrodes are uninsulated to provide electrical connection to the interior wall of the patient's airway.

Each of sense electrodes 82 and 83 includes a proximal end having positioning and locking hub 94, and is disposed for sliding movement through connector block 95. Connector block 95 permits a sliding electrical connection to be established between each sense electrode and the connector block, while permitting the sense electrodes to be moved proximally and distally therethrough. Plug 96 couples sense electrodes 82 and 83 to impedance recorder 110 via cable 97 electrically connected to connector block 95.

The interior of inflatable cuff 84 is in fluid communication with insufflation port 98 via lumen 88 of endotracheal tube 81. When inflated, inflatable cuff 84 retains endotracheal tube 81 in position within the patient's airway, thereby preventing inadvertent movement of the endotracheal tube. Inflatable cuff 84 also assists in urging sense electrodes 82 and 83 into contact with the interior wall of the trachea. Inflatable cuff 84 may be inflated using conventional inflation means (i.e., a liquid filled syringe or pressurized gas cylinder) connected to insufflation port 98 via lumen 88. Alternatively, inflatable cuff 84 may be replaced by another suitable type of expandable member for urging the sense electrodes against the interior wall of the patient's airway, such as an expanding mandrel, or other mechanical arrangement.

The proximal end of endotracheal tube 81, i.e., the end manipulated by the clinician, may include reference marks 99 on the circumference of the tube that reflect the circumferential orientation of electrodes 82 and 83 within the patient's trachea. The reference marks may be used to ensure proper registration of electrodes 82 and 83 with the portion of the tracheal wall nearest to the ascending aorta.

In an alternative embodiment of sense electrode apparatus of FIGS. 5 (not shown), more than two sense electrodes may be disposed on the endotracheal tube, so that the signals received from the electrodes may be optimally configured by the clinician after the endotracheal tube has been disposed in the patient's trachea. In this manner, a certain pair of the sense electrodes may be selected to provide an optimal output according to some predetermined metric, for example, the highest SNR. In such an embodiment, the impedance recorder or digital sampler may be modified to include suitable selection and switching logic, either as hardware or software, to select which sense electrodes contribute to the computed cardiac output.

Figures 6A, 6B:
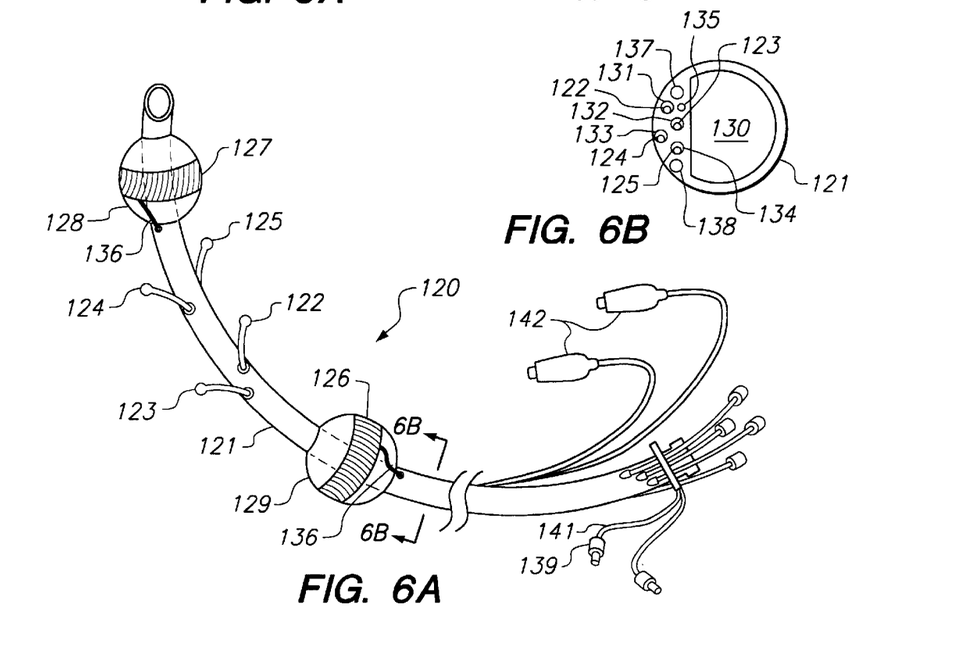
FIGS. 6A and 6B are, respectively, a perspective view and a cross-sectional view along view line 6B—6B, of an illustrative member of the second family of embodiments of the present invention.

Referring now to FIGS. 6A and 6B, an illustrative embodiment of apparatus 120 similar to that of apparatus 70 of FIG. 4C is described in greater detail. Apparatus 120 comprises endotracheal tube 121 carrying proximal sense electrodes 122 and 123, distal sense electrodes 124 and 125, and current electrodes 126 and 127 disposed on inflatable cuffs 128 and 129. As shown in FIG. 6B, endotracheal tube 121 includes lumen 130 for providing ventilation to the patient during intubation, lumens 131 and 132 through which proximal sense electrodes 122 and 123 may be reciprocated, lumens 133 and 134 through which distal sense electrodes 124 and 125 may be reciprocated, lumen 135 through which the electrical leads wires 136 for current electrodes 126 and 127 extend, and lumens 137 and 138 for inflating inflatable cuffs 128 and 129, respectively.

Sense electrodes are arranged so that, when fully deployed from their respective lumens, a line between the tips of electrodes 123 and 125 preferably forms an angle in a range of between 25 and 45 degrees with respect to the longitudinal axis of the endotracheal tube, thus approximating the angular orientation of the aortic anatomy. Also, a line between sense electrodes 122 and 124, when those electrodes are fully deployed, preferably is orthogonal to a line between electrodes 123 and 125. Apparatus 120 thereby permits determination of impedances "on-axis" and "normal-to-axis" as described with hereinabove with respect to FIG. 4C.

Sense electrodes 122–125 enter respective lumens 131–134 through openings near the proximal end of endotracheal tube 121, exit the respective lumens through skives that open to the lateral face of the endotracheal tube, and are reciprocable through the lumens in the same manner as sense electrodes 82 and 83 of the embodiment of FIGS. 5. Sense electrodes likewise are constructed as described above with respect to the embodiment of FIGS. 5, and are electrically coupled to plug 139 via connector block 140 and cable 141.

Inflatable cuffs 128 and 129 are in fluid communication with insufflation ports 142 via lumens 137 and 138 of endotracheal tube 121, and may be inflated as described above with respect to the embodiment of FIGS. 5. When inflated, inflatable cuffs 128 and 129 retain endotracheal tube 121 in position within the patient's airway, and serve to urge current electrodes 126 and 127 into electrical contact with the interior wall of the patient's airway.

Current electrodes 126 and 127 preferably comprise conductive foil strips about 6 to 10 cm in height, for example, Type M6001, available from the 3M Company, St. Paul, Minn., and may extend around the entire circumferences of inflatable cuffs 128 and 129, or may extend over only a portion of the circumference. The current electrodes may be disposed on the exterior of the inflatable cuffs using a suitable adhesive or fastening means. Proximal current electrode 126 is preferably connected to electrical ground. Alternatively, if inflatable cuffs 128 and 129 are eccentrically shaped, the current electrodes may be attached directly to the exterior of endotracheal tube 121.

The proximal end of endotracheal tube 121 may also include reference marks to assist in determining the circumferential orientation of the endotracheal tube within the patient's airway.

Figures 7A, 7B:
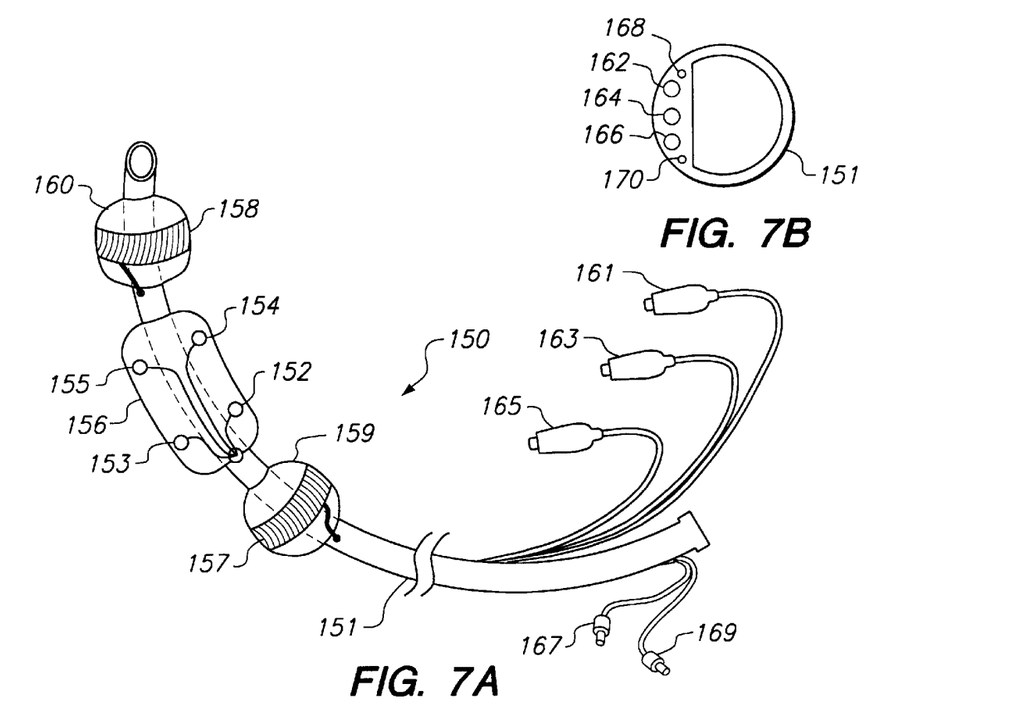
FIGS. 7A and 7B are, respectively, a perspective view and a cross-sectional view along view line 7B—7B, of an alternative member of the second family of embodiments of the present invention.

An alternative embodiment of the apparatus of FIGS. 6 is now described with respect to apparatus 150 of FIGS. 7A and 7B. Apparatus 150 comprises endotracheal tube 151 having proximal spot-type sense electrodes 152 and 153, and distal spot-type sense electrodes 154 and 155, disposed on elongate inflatable member 156, and current electrodes 157 and 158 disposed, respectively, on inflatable cuffs 159 and 160. In accordance with the high SNR aspect of the invention, a line between electrodes 153 and 154 preferably forms an angle α in a range of between 25 and 45 degrees with respect to the longitudinal axis of endotracheal tube 151, and orthogonal to a line between electrodes 152 and 155.

Elongate inflatable member 156 is inflated by insufflation port 161 via lumen 162 (see FIG. 7B), while inflatable cuffs 159 and 160 are inflated via insufflation port 163 and lumen 164, and insufflation port 165 and lumen 166, respectively. Electrical lead wires coupling current electrodes 158 and 159 to plug 167 are routed through lumen 168, while electrical lead wires coupling sense electrodes 152–155 to plug 169 are routed through lumen 170. Endotracheal tube 151 includes passageway 171 for providing ventilation and administering oxygen during intubation. The proximal end of endotracheal tube 121 may also include reference marks for determining the circumferential orientation of the endotracheal tube when inserted in the patient's airway.

When inflated, elongate inflatable member 156, which may be eccentric in shape, urges sense electrodes 152–155 into electrical contact with the interior of the patient's airway. Likewise, inflatable cuffs 159 and 160 urge current electrodes into electrical contact with the interior walls of the patient's airway at locations proximal and distal to elongate inflatable member 156.

Current electrodes 158 and 159 may comprise conductive foil strips of the type mentioned hereinabove, and may extend around the entire circumferences of inflatable cuffs 128 and 129, or may extend over only a portion of the circumference. Sense electrodes 152–155 may likewise be fashioned from conductive foil strips or from spot-type EKG electrodes, also as described hereinabove. The current and sense electrodes are fastened to the exterior of the inflatable member and cuffs using a suitable adhesive or fastening means.

Operation of any of the above-described embodiments of the present invention is now briefly described. First, the endotracheal tube is inserted into the patient through the nasal cavity, past the epiglottis and into the trachea in accordance with standard intubation practice. If the apparatus of the present invention is to be used for only a relatively short period of time, e.g., while a patient is anesthetized during surgery, an endotracheal tube alternatively may be inserted into the trachea via the mouth. Alternatively, access to the trachea may be had through a surgical opening at the suprasternal notch by conventional tracheotomy.

Using the reference marks on the circumference of the proximal end of the endotracheal tube (if present), the clinician may manipulate the endotracheal tube to ensure proper orientation of the endotracheal tube within the patient's airway. The inflatable cuff or cuffs then are inflated to stabilize the endotracheal tube, and the hubs of the sense electrodes are moved distally to deploy the sense electrodes into electrical contact with the interior wall of the patient's trachea and/or bronchus (or for the embodiment of FIGS. 7, the elongate inflatable member is inflated). The current electrodes are either urged into contact with the interior of the patient's airway, by inflating the inflatable cuffs, or are separately applied to the external surface of the patient. The sense electrodes (optionally including the external sense electrode) and current electrodes are then connected to impedance recorder 110. Bioelectrical impedance values may be then determined for processing as described hereinbelow.

Figure 8:
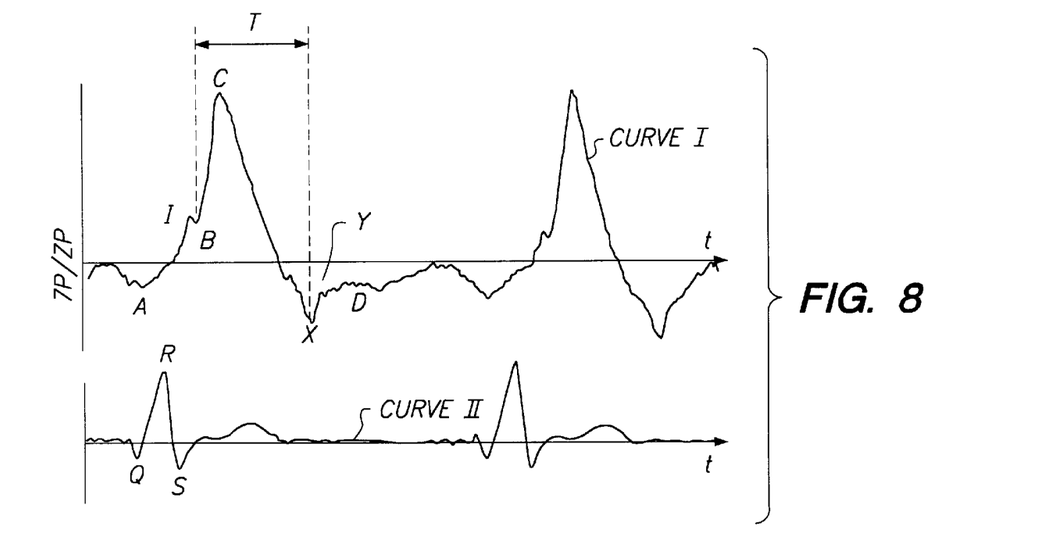
FIG. 8 is a graph showing the relationship between cardiac events and the first derivative of the bioelectrical impedance.

A method of computing cardiac output in accordance with the well-known Kubicek equation is now described. Referring to FIG. 8, the first derivative of the measured impedance (dZ/dt) (curve I) is compared to a typical electrocardiograph waveform (curve II) for a normal patient, where the components of the waveform describing events within the cardiac cycle are labeled. Curve I includes an A-wave component, due to atrial activity at the beginning of the cardiac cycle, represented by a downward deflection in the curve. The I-wave component represents an upward deflection in curve I occurring during isometric contraction. The B-wave component corresponds to the start of blood flow out of the ventricles, while the C-wave component of curve I represents the major upward deflection during the cardiac cycle. The amplitude of this deflection, measured from the zero point, is used in the calculation of the ventricular stroke volume ("SV"). The X and Y points of curve I reflect closure of the aorta and pulmonary valves, respectively. Point O corresponds to rapid filling of the ventricles.

SV is calculated according to equation (4) as:

$$SV = \rho (L/Z_0)^2 * (dZ/dt_p) \tau \qquad (4)$$

where:

SV=ventricular stroke volume, ml;

ρ=resistivity of blood (in normal patients, about 150–200 ohm-cm/s, and can be corrected for each patient as a function of hematocrit);

L=distance between the sense electrodes, cm;

$Z_0$=mean impedance between the measurement electrodes, ohms;

$dZ/dt_p$=peak value of the upward deflection in the first derivative of the impedance waveform (amplitude of C-wave); and τ=ventricular ejection time (computed as the period between the occurrence of the B-wave component and point X in curve I).

The digitized first derivative of the impedance determined by the impedance recorder is analyzed to extract the B-wave and C-wave components and the X deflection point. The amplitude of the B-C-X portion of the curve I waveform, and the time between these segments are then employed to compute stroke volume using equation (4). The distance between the electrodes L is either known as a manufacturing parameter (where the sense electrodes are all on the endotracheal tube) or may be computed based on external dimensions (where an external sense electrode is employed, as in FIG. 3A).

In a preferred embodiment of the invention, SV is continuously computed for each data segment that is of good signal quality, i.e., where the amplitude of the derivative of the impedance signal is above a certain quality metric. The SV may be continuously updated on a display (not shown) associated with computer 114, and may consist of a running average of the current and a user-selectable number of preceding cardiac cycles. Cardiac output may then be computed as the product of the instantaneous average SV and the heart rate, and also displayed numerically.

Alternatively and in accordance with the methods of the present invention, equations for computing cardiac output using the apparatus of the present invention may be derived as follows:

The cross-sectional area, a, of a cylindrical vessel may be computed as:

$$a=(1/Z-1/Z_0)\rho L=(\Delta Z/ZZ_0)\rho L \approx \Delta Z \rho L/Z_0^2 \qquad (5)$$

where Z is the measured electrical impedance; $Z_0$ is the baseline electrical impedance; $\rho$ is the resistivity of blood (typically 150–200 ohm-cm); L is the spacing between the sense electrodes; and $\Delta Z = Z - Z_0$.

The instantaneous flow of blood, Q, through blood vessels of cross-sectional area a may be computed from:

$$Q = a^2 P/8 \Pi L \eta \qquad (6)$$

where $\eta$ is the dynamic viscosity of blood, P is the average blood pressure drop along the blood vessel (a linear function of the maximum difference during the cardiac cycle) and L is the inter-electrode spacing.

Cardiac Output ("CO") therefore may be computed by integrating Q over predefined intervals (e.g., one minute intervals):

$$CO = \int Q dt \qquad (7)$$

Applicant has observed that even in the simple parallel cylindrical model referred to in FIG. 1B, the relation between impedance changes and cardiac output is complex and dependent on the electrode configuration as well as multiple time-varying physiological parameters. Known bio-impedance algorithms, such as the Kubicek equation (equation (4)), when used with previously known apparatus, do not account for this complexity, and therefore have achieved limited clinical use.

In accordance with the present invention, however, the sense electrodes may be disposed in close proximity to the ascending aorta, which initial testing has shown to provide a sharp and reproducible waveform that linearly tracks the ascending aorta blood flow waveform (as determined by an implanted flow meter). This linear time-varying (i.e., with cardiac cycle) relationship between blood flow and impedance change may be described as:

$$Q(t) = T(G, Z_0, t) \Delta Z(t) \qquad (8)$$

where Q is the computed blood flow; T is a transfer function; G is a constant dependent upon the inter-electrode spacing and size of the electrodes; and t is the time interval relative to the cardiac cycle (e.g., the p wave of the EKG).

The transfer function T of equation (8) is empirically derived from in-vivo experiments in patients with in-dwelling flow probes and continuous impedance measurements. A look-up table, LUT(t), is generated from the above-described experiments and is used to estimate the instantaneous flow Q. CO is then calculated based on the integral of Q over, for example, a one minute period, or by integrating the ensemble average of one cardiac cycle and multiplying by the heart rate:

$$CO \approx K/Z_0^2 \int LUT(t) \Delta Z(t) dt \qquad (9)$$

where K is an empirically-derived constant.

Further alternative embodiments of the present invention also may include additional sensors to enable other types of quantitative analysis. For example, diodes suitable for employing blood oximetry techniques based on near infrared light absorption also may be disposed on the endotracheal tube to measure blood oxygen saturation levels. In particular, multiple light emitting diodes, including one or more red-light and infrared emitting diodes, may be disposed on the endotracheal tube, on the inflatable cuff or member, or both, for obtaining blood oxygen saturation measurements using transreflectance oximetry techniques, as described, for example, in U.S. Pat. No. 5,099,842, the entirety of which is incorporated herein by reference.

Figure 9A:
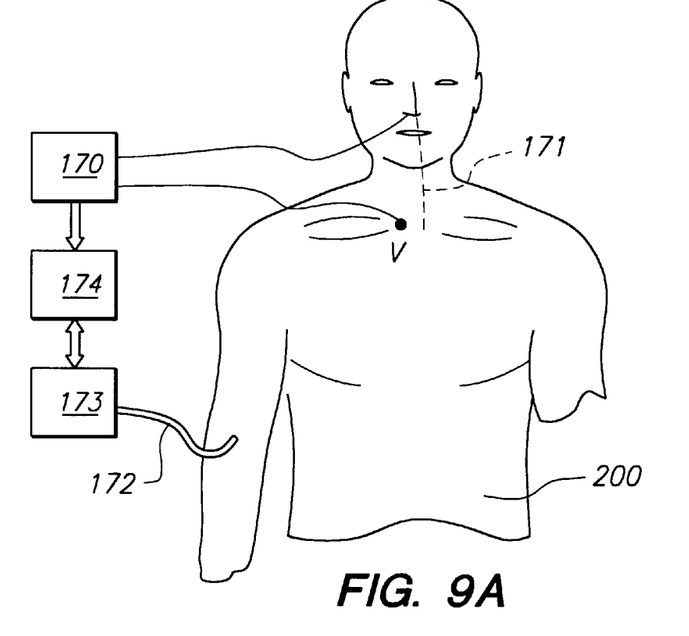
FIGS. 9A and 9B are, respectively, schematic diagrams showing systems for administering fluids to a patient and for controlling heart rate for patients having pacemakers, respectively, constructed in accordance with the principles of the present invention.

Referring now to FIG. 9A, use of the apparatus of the present invention is described as a controller for fluids administration. In FIG. 9A, cardiac output is measured by apparatus 170, which may be any of the foregoing embodiments, and includes endotracheal tube 171 disposed in patient 200. Apparatus 170 is used to monitor hemodynamic status and as a metric to control the administration of fluids intravenously via lumen 172 coupled to fluid supply system 173. Computer 174, which may be an IBM-compatible PC (and, for example, the same computer that computes cardiac output from the impedance values output by impedance recorder 110 and digital sampler 112), controls fluid supply system 172.

Operation of the apparatus of FIG. 9A is as follows. After a one unit loss of blood, for example, it is known that cardiac output changes but that heart rate and blood pressure do not. Thus, decreased cardiac output can be used to monitor the amount of fluids to be given to a patient. The apparatus of FIG. 9A provides a closed-loop system wherein the amount of fluid injected into the patient is controlled by the cardiac output computed as described hereinabove. In particular, a baseline cardiac output measurement is obtained and then a bolus of 50 cc of fluid is given while cardiac output is measured continuously. As long as the cardiac output increases, additional boluses of fluid are given periodically, e.g., every 15 minutes. This process may be repeated several times a day for a critically ill patient.

Figure 9B:
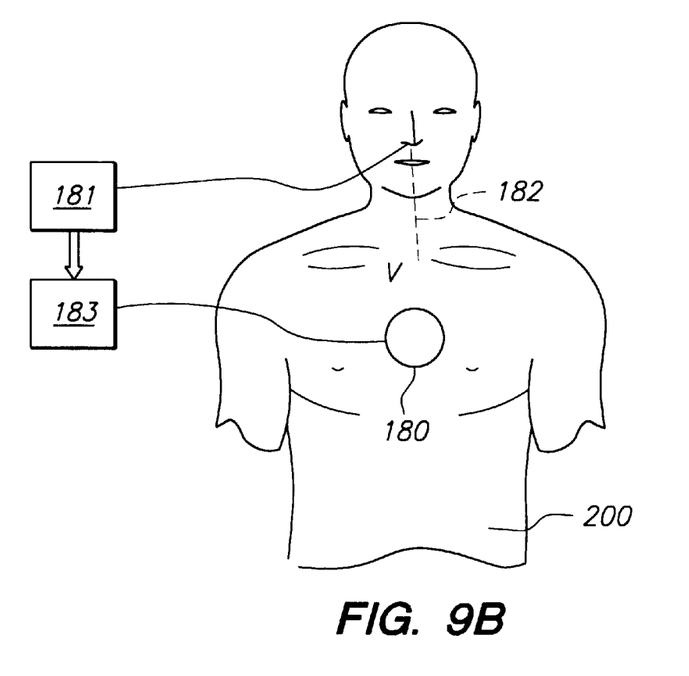

Referring now to FIG. 9B, use of the apparatus of the present is described as a controller for pacemaker 180. Generally, it is desirable to maximize cardiac output for the lowest possible heart rate, since the lower the heart rate, the lower the myocardial oxygen consumption. In the arrangement of FIG. 9B, cardiac output is measured by apparatus 181, which may be any of the foregoing embodiments, and includes endotracheal tube 182 disposed in patient 200. The output of apparatus 181 is used, in conjunction with computer 183, as a metric to control the setting of pacemaker 180 as described hereinafter.

A baseline cardiac output measurement is first obtained and then the heart rate is reduced by a predetermined amount, e.g., two beats/min, while the cardiac output is continuously monitored by apparatus 181. As long as the cardiac output increases or remains unchanged, the heart rate is periodically further lowered by the predetermined amount, for example, by 2 beats/min every 15 minutes. The process of reducing heart rate while monitoring cardiac output is continued until either a minimum desired heart rate is obtained or the cardiac output measured by apparatus 181 begins to decrease. If the cardiac output is determined to have decreased, the heart rate is returned to the preceding higher rate.

Initial testing of the methods and apparatus constructed in accordance with the present invention has yielded results comparable to catheterization techniques, but with a continuous output. Animal tests have been conducted using an implanted occluder within the inferior vena cava to vary preload and a Doppler ultrasound flow probe implanted on the ascending aorta to obtain samples for correlation to the output of the bio-impedance recorder. Good correlation of the Doppler measurements to the bio-impedance determined with apparatus similar to that of FIG. 4A has been obtained. In addition, no damage to tracheal mucosa has been observed, even after extended periods of intubation.

Although preferred illustrative embodiments of the invention are described above, it will be obvious to one skilled in the art that various changes and modifications may be made therein without departing from the invention and that the appended claims are intended to cover all such changes and modifications which fall within the true spirit and scope of the invention. For example, applicant expects that the apparatus and methods of the present invention may be advantageously applied to animal subjects employed in clinical studies, as well as humans.

What is claimed is:

1. Apparatus for computing a metric corresponding to a patient's cardiac output, the apparatus comprising:
   a bioelectrical impedance recorder;
   an endotracheal tube having a proximal portion, a distal portion, and a longitudinal axis, the endotracheal tube is adapted to be inserted in the trachea of the patient through one of the mouth, a nasal passageway, or a tracheotomy port;
   first and second sense electrodes disposed on the distal portion and electrically coupled to the bioelectrical impedance recorder, the first and second sense electrodes spaced apart a first distance along the longitudinal axis;
   means for urging the first and second sense electrodes against an interior wall of the patient's airway;
   first and second current electrodes electrically coupled to the bioelectrical impedance recorder for injecting a current into the patient's thorax, the first and second current electrodes spaced apart a second distance greater than the first distance,
   wherein the first and second sense electrodes generate a signal corresponding to the bioelectrical impedance of blood flow through the aorta and the signal is provided to the bioelectrical impedance recorder.

2. The apparatus as defined in claim 1 further comprising an external sense electrode coupled to the bioelectrical impedance recorder, one of the first and second sense electrodes and the external sense electrode generating an alternate signal corresponding to the bioelectrical impedance of blood flow through the aorta, the alternate signal being provided to the bioelectrical impedance recorder.

3. The apparatus as defined in claim 1 wherein at least one of the first and second current electrodes are disposed on the endotracheal tube.

4. The apparatus as defined in claim 1 wherein the first and second sense electrodes are arranged so that a line intersecting the first and second sense electrodes forms an angle α relative to the longitudinal axis of the endotracheal tube.

5. The apparatus as defined in claim 4 wherein the angle α is a range of 25 to 45 degrees.

6. The apparatus as defined in claim 4 wherein the second sense electrode is disposed distal to the first sense electrode, the apparatus further comprising a third sense electrode disposed distal to, but circumferentially spaced apart from, the first sense electrode and a fourth sense electrode disposed proximal to, but circumferentially spaced apart from, the second sense electrode, so that a line intersecting the third and fourth sense electrodes is orthogonal to a line intersecting the first and second sense electrodes.

7. The apparatus as defined in claim 1 wherein the endotracheal tube comprises at least first and second lumens, the first and second sense electrodes comprising first and second wires disposed for sliding movement through the first and second lumens, respectively.

8. The apparatus as defined in claim 7 wherein the first and second wires include pre-stressed portions that cause the first and second sense electrodes to deflect outwardly when extended from the first and second lumens, respectively, the pre-stressed portions constituting the means for urging.

9. The apparatus as defined in claim 1 wherein the endotracheal tube further comprises an expandable member for retaining the endotracheal tube at a desired location in the passageway.

10. The apparatus as defined in claim 9 wherein the expandable member constitutes the means for urging.

11. The apparatus as defined in claim 10 wherein the first and second sense electrodes are disposed upon the expandable member.

12. The apparatus as defined in claim 9 wherein the expandable member is an inflatable cuff, and the endotracheal tube further comprises a lumen for inflating the inflatable cuff.

13. The apparatus as defined in claim 1 wherein at least one of the first and second current electrodes is disposed on an inflatable cuff.

14. The apparatus as defined in claim 1 wherein the apparatus further comprises reference marks on the proximal end of the tube to determine circumferential orientation of the endotracheal tube within the patient's trachea.

15. The apparatus as defined in claim 1 further comprising a fluid administration system for injecting a bolus of fluid into the vascular system of the patient, the fluid administration system coupled to the circuitry for processing and responsive to the metric corresponding to the cardiac output.

16. The apparatus as defined in claim 1 further comprising a pacemaker controlling the heart rate of the patient, the pacemaker coupled to the circuitry for processing and responsive to the metric corresponding to the cardiac output.

17. A method of measuring the cardiac output of an organism comprising steps of:
    providing a bioelectrical impedance recorder;
    providing an endotracheal tube having first and second sense electrodes disposed thereon, the first and second sense electrodes spaced apart a first distance;
    inserting the endotracheal tube in the trachea of the organism through a nasal passageway, the mouth of the organism, or a tracheotomy port to position first and second sense electrodes within an airway of the organism in the vicinity of the ascending aorta;
    coupling first and second current electrodes to inject a current into the thorax of the organism, the first and second current electrodes spaced apart a second distance greater than the first distance;
    applying a voltage from the bioelectrical impedance recorder between the first and second current electrodes so that a current flows through the tissues of the organism disposed along the second distance between the first and second current electrodes; and
    detecting with the bioelectrical impedance recorder a voltage developed across the first and second sense electrodes caused by the current flowing in the tissues of the organism, the voltage varying in accordance with changes in the bioelectrical impedance of the tissues.

18. The method as defined in claim 17, further comprising a step of aligning the first and second sense electrodes with an axis of the ascending aorta of the organism.

19. The method as defined in claim 17, wherein the step of positioning the first and second current electrodes comprises a step of positioning the first and second current electrodes on an external surface of the organism.

20. The method as defined in claim 17 wherein the steps of applying a voltage between the first and second current electrodes and detecting a voltage developed across the first and second sense electrodes are performed continuously.

21. The method as defined in claim 17, further comprising steps of:
providing a fluid administration system for injecting a bolus of fluid intravenously into the organism's vascular system;
periodically actuating the fluid administration system responsive to the detected voltage developed across the first and second sense electrodes.

22. The method as defined in claim 21, wherein the step of periodically actuating the fluid administration system is performed every 15 minutes only while the cardiac output is measured to be increasing.

23. The method as defined in claim 17 further comprising steps of:
providing a pacemaker electrically coupled to the heart of the organism to control heart rate; and
adjusting the heart rate responsive to voltage developed across the first and second sense electrodes to optimize cardiac output.

24. The method as defined in claim 23, wherein the step of adjusting the heart rate comprises a step of lowering the heart rate to obtain either a predetermined minimum heart rate or until the cardiac output is measured to be decreasing.

25. Apparatus for computing a metric corresponding to a patient's cardiac output, the apparatus comprising:
a bioelectrical impedance recorder,
an endotracheal tube having a proximal portion, a distal portion, and a longitudinal axis;
first and second sense electrodes disposed on the distal portion and electrically coupled to the bioelectrical impedance recorder, the first and second sense electrodes spaced apart a first distance along the longitudinal axis;
means for urging the first and second sense electrodes against an interior wall of the patient's airway;
first and second current electrodes electrically coupled to the bioelectrical impedance recorder for injecting a current into the patient's thorax, the first and second current electrodes spaced apart a second distance greater than the first distance, at least one of the first or second current electrodes disposed on the endotracheal tube,
wherein the first and second sense electrodes generate a signal corresponding to the bioelectrical impedance of blood flow through the aorta and the signal is provided to the bioelectrical impedance recorder.

26. The apparatus as defined in claim 25, wherein the second sense electrode is disposed distal to the first sense electrode, the apparatus further comprising a third sense electrode disposed distal to, but circumferentially spaced apart from, the first sense electrode and a fourth sense electrode disposed proximal to, but circumferentially spaced apart from, the second electrode, so that a line intersecting the third and fourth sense electrodes is orthogonal to a line intersecting the first and second sense electrodes.

27. The apparatus as defined in claim 26, wherein the first and second sense electrodes are arranged so that a line intersecting the first and second sense electrodes forms an angle α relative to the longitudinal axis of the endotracheal tube.

28. The apparatus as defined in claim 25, wherein the endotracheal tube further comprises an expandable member for retaining the endotracheal tube at a desired location in the passageway.

29. The apparatus as defined in claim 28 wherein the expandable member constitutes the means for urging.

30. The apparatus as defined in claim 29, wherein the first and second sense electrodes are disposed upon the expandable member.

31. The apparatus as defined in claim 30, wherein the expandable member is an inflatable cuff, and the endotracheal tube further comprises a lumen for inflating the inflatable cuff.

32. The apparatus as defined in claim 25, wherein at least one of the first and second current electrodes is disposed on an inflatable cuff.

33. Apparatus for computing a metric corresponding to a patient's cardiac output, the apparatus comprising:
a bioelectrical impedance recorder;
an endotracheal tube having a proximal portion, a distal portion, and a longitudinal axis;
first, second, third and fourth sense electrodes disposed on the distal portion and electrically coupled to the bioelectrical impedance recorder, the first and second sense electrodes spaced apart a first distance along the longitudinal axis, the third and fourth sense electrodes circumferentially spaced apart so that a line intersecting the first and second sense electrodes is substantially orthogonal to a line intersecting the third and fourth sense electrodes;
means for urging the first, second, third and fourth electrodes against an interior wall of the patient's airway;
first and second current electrodes electrically coupled to the bioelectrical impedance recorder for injecting a sense current into the patient's thorax, the first and second current electrodes spaced apart a second distance greater than the first distance,
wherein the first, second, third and fourth sense electrodes generate a signal corresponding to the bioelectrical impedance of blood flow through the aorta and the signal is provided to the bioelectrical impedance recorder.

34. The apparatus as defined in claim 33 wherein at least one of the first and second current electrodes is disposed on the endotracheal tube.

35. The apparatus as defined in claim 33, wherein the second sense electrode is located circumferentially away from the first sense electrode, so that a line intersecting the first and second sense electrodes forms an angle α relative to the longitudinal axis of the endotracheal tube.

36. The apparatus as defined in claim 33, wherein the endotracheal tube further comprises an expandable member for retaining the endotracheal tube at a desired location in the passageway.

37. The apparatus as defined in claim 36, wherein the expandable member constitutes the means for urging.

38. The apparatus as defined in claim 37, wherein the first and second sense electrodes are disposed upon the expandable member.

* * * * *